United States Patent
Oomura et al.

(10) Patent No.: US 6,342,256 B1
(45) Date of Patent: Jan. 29, 2002

(54) TOFU PRODUCTS EXCELLENT IN FREEZE RESISTANCE AND PROCESS FOR PRODUCING THE SAME

(75) Inventors: Hiroki Oomura; Tomohiko Adachi; Shin Nakatani; Takeshi Akasaka, all of Kobe (JP)

(73) Assignee: Fuji Oil Company, Limited, Osaka (JP)

(*) Notice: Subject to any disclaimer, the term of this patent is extended or adjusted under 35 U.S.C. 154(b) by 0 days.

(21) Appl. No.: 09/763,367
(22) PCT Filed: Oct. 13, 1999
(86) PCT No.: PCT/JP99/05635
§ 371 Date: Feb. 21, 2001
§ 102(e) Date: Feb. 21, 2001
(87) PCT Pub. No.: WO00/21389
PCT Pub. Date: Apr. 20, 2000

(30) Foreign Application Priority Data

Oct. 13, 1998 (JP) ............................. 10-290912

(51) Int. Cl.$^7$ .................................. A23L 1/20
(52) U.S. Cl. .......................... 426/46; 426/634
(58) Field of Search ..................... 426/634, 46

(56) References Cited

FOREIGN PATENT DOCUMENTS

| | | |
|---|---|---|
| JP | 3-61463 | 3/1991 |
| JP | 6-113777 | 4/1994 |
| JP | 6-217729 | 8/1994 |
| JP | 6-269257 | 9/1994 |
| JP | 7-194331 | 8/1995 |
| JP | 9-94075 | 4/1997 |
| JP | 9-182571 | 7/1997 |
| JP | 9-313125 | 12/1997 |
| JP | 10-99040 | 4/1998 |
| JP | 10-127247 | 5/1998 |

*Primary Examiner*—Anthony J. Weier
(74) *Attorney, Agent, or Firm*—Wenderoth, Lind & Ponack, LLP

(57) ABSTRACT

A process for industrially producing tofu products which are excellent in taste and freeze resistance. This process involves concentrating soybean milk extracted from uncooked soybean slurry or puree; adding one or more members selected from sugars, starch and transglutaminase to the concentrated soybean milk at an elevated temperature; adding a solidifying agent to prepare tofu; further heating the tofu in two steps; and then freezing.

9 Claims, No Drawings

TOFU PRODUCTS EXCELLENT IN FREEZE RESISTANCE AND PROCESS FOR PRODUCING THE SAME

This application is a 371 of PCT/JP99/05635 filed Oct. 13, 1999.

ART FIELD RELATED

The present invention relates to frozen tofu products, and their production. Tofu (soybean curd) products [e.g., tofu, atsuage (thick fried tofu), etc.] have heretofore been said to be difficult to store for a long period of time, and have also been said to be difficult to subject to freezing storage. However, even when the tofu products of the present invention are frozen, and stored for a prescribe period of time, they are scarcely denatured by freezing. Further, when they are thawed and cooked for eating, they have excellent taste and cooking applicability, and are smooth.

PRIOR ART

As is generally known, tofu is produced by soaking soybeans in water for a certain period of time, grinding the soybeans, adding water thereto, heating the resultant slurry or puree and separating okara (soy pulp or tofu waste) to obtain hot soybean milk. To this soybean milk, a solidifying agent (coagulant) is added to obtain tofu. When this tofu is frozen, spongy tissue or layered tissue such as frozen tofu (kōya tofu) is formed, thereby spoiling smooth mouthfeel before freezing. Then, various examinations are carried out to improve this.

For example, JP 6-217729 A and JP 6-269257 A propose processes for producing tofu having freeze resistance, wherein transglutaminase, starch and the like are added to soybean milk. However, when tofu is produced by these processes in a large scale, it is very difficult to control a coagulation reaction because of the increase in viscosity of soybean milk, and there are problems in the production of tofu having good tissue.

In addition, JP 9-182571 A proposes a process for producing frozen tofu, wherein starch and the like are added to soybean milk concentrated to 14% to 20%. However, unless a solidifying agent is added to soybean milk at a temperature of 30° C. or lower, taste and mouthfeel of tofu cannot be improved because of the increase in viscosity. Then, at present, an industrial process which can stably produce tofu having excellent freeze resistance is not yet established.

Further, after thawing frozen tofu stored for a prescribed period of time, cooking applicability of thawed tofu is spoiled and, when a lot of tofu are cooked in a large batch, they are crumbled or broken. A process for producing tofu maintaining excellent cooking applicability after thawing and cooking is not yet established.

DISCLOSURE OF THE INVENTION

Problems to be Solved by the Invention

As described hereinabove, a method for efficiently improving freeze resistance of tofu does not yet become popular. The present inventors have studied freeze resistance of tofu. Thus, the present invention is to provide a process for industrially producing frozen tofu products which are not denatured even by freezing, and have the same mouthfeel and taste as those of fresh tofu even after thawing, and are excellent in cooking applicability.

Means for Solving the Problems

The present invention is tofu products having freeze resistance obtainable by adding one or more members selected from the group consisting of sugars, starch and transglutaminase to soybean milk having low viscosity and a solids content of at least 10%; adding a solidifying agent to prepare tofu; and then freezing. The present invention also provides a process for producing the tofu products.

More specifically, in order to obtain soybean milk having low viscosity, concentrated soybean milk having low viscosity and a high solids content can be produced by extracting soybean milk from uncooked soybean slurry or puree prepared from whole soybeans, and concentrating the soybean milk so that the solids content after heating becomes 10% to 16%. To this concentrated soybean milk, 0.1 to 5% by weight of the sugars or starch, or 0.01 to 2% by weight of transglutaminase, and the solidifying agent are added at the temperature of the concentrated soybean milk of 60° C. or higher to prepare tofu. The tofu is heated to elevate its temperature stepwise to obtain tofu having elasticity. The tofu thus obtained has freeze resistance and is excellent in cooking applicability.

EMBODIMENTS OF THE INVENTION

Hereinafter, the present invention will be illustrated in detail. In the process for producing tofu products having excellent freeze resistance of the present invention, it is better to heat and concentrate uncooked soybean milk extracted from fresh soybean slurry or puree to obtain concentrated soybean milk having low viscosity and a high solids content. Further, in order to obtain tofu having excellent elasticity, preferably, the additive and the solidifying agent are added to the above concentrated soybean milk wormed to 60° C. or higher, followed by further heating the mixture stepwise (e.g., two steps) to elevate the temperature.

In a conventional process for producing tofu, generally, soybean milk is extracted from cooked soybean slurry or puree. That is, soaked soybeans are ground together with water to obtain soybean slurry or puree. The soybean slurry or puree is heated with live steam, followed by separating okara therefrom to obtain soybean milk. When soybean slurry or puree is treated by heating in this manner, viscosity of the soybean milk is increased, which adversely affects on the subsequent coagulation reaction.

In contrast, in the present invention, soybean milk is extracted from uncooked soybean slurry or puree. That is, soaked soybeans are ground together with water to obtain soybean slurry or puree. Okara is separated from the soybean slurry or puree to obtain uncooked soybean milk. This is concentrated by heating (at 90° C. or higher for 5 minutes or more). The resultant concentrated soybean milk has low viscosity, while it has a high solids content. It has been confirmed that good tofu is obtained by the subsequent coagulation reaction of this concentrated soybean milk. The term "low viscosity" used herein means that viscosity of soybean milk at 10° C. is not higher than 100 mPa·s or lower, preferably, 50 mPa·s or lower.

The concentration method is not limited to a specific one. For example, good concentrated soybean milk can efficiently be obtained by heat concentration under reduced pressure with a centrifugal thin membrane because excessive heating of soybean milk can be avoided. In the present invention, preferably, the solids content of soybean milk is adjusted to 10 to 16% by weight. When the solids content is less than 10% by weight, mouthfeel of the resultant tofu becomes inferior, and tends to be denatured after freezing. When the solids content is over 16% by weight, viscosity of soybean milk is rapidly increased and it is difficult to subject the soybean milk to an appropriate coagulation reaction.

Therefore, it is necessary to adjust the concentration of soybean milk within the above range.

Next, to the concentrated soybean milk obtained by the above method, one or more members selected from the group consisting of sugars, starch and transglutaminase are added to prevent freeze denaturation.

Examples of sugars include sucrose, fructose, xylose, sorbitol and the like, with oligosaccharides having low sweetness, sugar alcohol such as erythritol, maltitol, etc., trehalose, and the like being preferred.

Starch may be cereal starch such as corn starch, wheat flour starch, etc., and their processed products such as α-starch, oxidized starch, etc., with starch which has freeze resistance without syneresis being preferred.

Transglutaminase is an enzyme normally obtained by culturing a microorganism with starch, etc. as a fermentative raw material, and is an outstanding enzyme for crosslinking proteins in food to produce a close and smooth texture. In the present invention, a transglutaminase preparation containing an edible material such as starch, etc. may be used.

The temperature of the soybean milk at which the solidifying agent are added the concentrated soybean milk is preferably 60° C. or higher. Although bad taste of soybean milk can be somewhat improved by the above concentration, if the temperature is lower than 60° C., sufficient improvement of taste is scarcely expected and the resultant product has less specific taste of tofu and less elasticity. This may be due to a too slow reaction between proteins in soybean milk and the solidifying agent. Further, in case of addition of starch, when the temperature is higher than 70° C., viscosity of soybean milk is rapidly increased due to gelatinization of starch and it is difficult to subject soybean milk to an appropriate coagulation reaction. Then, attention should be given to the temperature of soybean milk.

The solidifying agent to be used in the present invention includes a bittern normally used in the tofu production, calcium salts such as calcium sulfate, etc., magnesium salts such as magnesium chloride, glucono delta-lactone and the like, with calcium sulfate whose a coagulation reaction is gentle being preferred.

Next, the tofu produced above is aged at 60 to 70° C. for 10 to 60 minutes so that transglutaminase acts on the tofu, and the coagulation reaction with the solidifying agent becomes gentle to facilitate the stable production of the tofu. Then, the tofu is heated to elevate its temperature stepwise to inactivate transglutaminase and to promote the coagulation reaction in the tofu to provide elasticity. When the latter heating is carried out in combination with the above heating at 60 to 70° C. by 2 steps, the tofu is heated at 80 to 90° C. for 10 to 60 minutes. If the final heating is carried out at lower than 80° C., transglutaminase is insufficiently inactivated and elasticity of the tofu is also insufficient. If the heating is carried out at higher than 90° C., the tofu tissue is spongy and its mouthfeel is inferior.

Then, the tofu is cut into a prescribed size. After cooling to 40° C. or lower, the tofu is frozen with a quick freezer. Alternatively, after cutting into a prescribed size, the tofu may be fried to prepare so-called "atsuage" and then quickly frozen. The frozen tofu products thus obtained can keep the mouthfeel of tofu for more than 6 months.

In addition, cooking applicability such as a lot of tofu can be cooked in a large batch without crumbling or breaking is desired in a market of tofu for business use, where there are much opportunity that a lot of tofu are cooked in a large batch such as meals for schoolchildren, workers, etc.

EXAMPLES

The advantages of the present invention will be illustrated by the following examples but they are not to be construed to limit the technical ideas of the present invention.

Example 1

Water (10° C.) (15 kg) was added to whole soybeans (5 kg) and the soybeans was soaked in water for 14 hours. The mixture was separated into soaking whey and soaked soybeans with a 10 mesh sieve. Then, the soaked soybeans were ground together with water for grinding (20° C.) (25 kg) by a grinder (manufactured by Nakagawa Kikai Seisaku-sho, hereinafter used the same grinder) to obtain soybean slurry. The slurry was separated into soybean milk (solids concentration: 9% by weight) and okara by a separator (manufactured by K.K. Tofer, hereinafter used the same separator).

The soybean milk was heated at 98° C. for 5 minutes by a indirect heating apparatus (manufactured by K.K. Hoshidaka, hereinafter used the same apparatus).

The resultant soybean milk was adjusted to the solids concentration of 14% by weight by a concentrator (manufactured by K.K. Hisaka Seisaku-sho, hereinafter used the same concentrator) under vacuum of 100 torr. Viscosity of the resultant soybean milk was measured at 10° C. with a viscometer (manufactured by TOKIMEC K.K., hereinafter used the same viscometer).

Next, the concentrated soybean milk was adjusted to 70° C. and, to this, calcium sulfate (0.3% by weight), potato starch (2% by weight, manufactured by Sanwa Starch K.K., hereinafter used the same starch) and a transglutaminase preparation (0.1% by weight, manufactured by Ajinomoto K.K., hereinafter used the same preparation) were added. The mixture was placed in a molding box (length: 150 mm, width: 100 mm and depth: 30 mm, hereinafter used the same box). After standing for about 10 minutes, the box was heated with a steamer at 90° C. for about 20 minutes to produce tofu. This was cut into a prescribed size and, after cooling to 40° C. or lower, the tofu was quickly frozen in an atmosphere at −35° C.

Example 2

According to the same manner as described in Example 1, tofu was prepared except that the soybean milk separated by the separator was concentrated to the solids concentration of 11% by weight.

Example 3

According to the same manner as described in Example 1, tofu was prepared except that the soybean milk separated by the separator was concentrated to the solids concentration of 16% by weight.

Example 4

According to the same manner as described in Example 1, tofu was prepared except that the amount of starch to be added to the concentrated soybean milk adjusted to 70° C. was 0.2% by weight.

Example 5

According to the same manner as described in Example 1, tofu was prepared except that the amount of transglutaminase to be added to the concentrated soybean milk adjusted to 70° C. was 0.01% by weight.

Comparative Example 1

According to the same manner as described in Example 1, tofu was prepared except that 32 kg of water for grinding was used, and soybean milk separated by the separator was adjusted to the solids concentration of 6% by weight and used without concentration.

Comparative Example 2

According to the same manner as described in Example 1, tofu was prepared except that the concentrated soybean milk was adjusted to 30° C. and, after addition of the additives and the solidifying agent, the soybean milk was heated at 60° C. for 30 minutes and further at 90° C. for 30 minutes by the steamer.

Comparative Example 3

According to the same manner as described in Example 1, tofu was prepared except that the concentrated soybean milk was adjusted to 80° C. and, after addition of the additives and the solidifying agent, the soybean milk was held for 10 minutes.

Comparative Example 4

The soybean slurry prepared with the grinder in Example 1 was heated with a steam heating pan (manufacture by K.K. Tofer, hereinafter used the same pan) and the soybean slurry was separated into cooked soybean milk (solids concentration 9% by weight) and okara by the separator. According to the same manner as described in Example 1, the resultant soybean milk was concentrated to prepare tofu.

Comparative Example 5

According to the same manner as described in Comparative Example 4, tofu was prepared except that the concentrated soybean milk was adjusted to 30° C. and, after addition of the same additives and solidifying agent as in Comparative Example 4, the soybean milk was heated at 60° C. for 30 minutes with a steamer, followed by heating at 90° C. for 30 minutes.

Summary of Conditions in Examples and Comparative Examples and Results of Measurement and Evaluation The separation of soybean milk is represented by extraction of uncooked soybean slurry (U) or cooked soybean slurry (C).

The measurement of solids concentration of soybean milk was carried out by an apparatus for measuring loss in weight on drying (105° C. for 4 hours).

Viscosity was measured by a viscometer.

The state of coagulation reaction of soybean milk was evaluated by observation with naked eyes of skilled persons. The results are shown by O (uniform gelation) and X (crumbled gel or no gelation).

Cooking applicability was evaluated by observation of states of crumbling with naked eyes of skilled cooks after cooking the frozen tofu in given stock for about 1 hour. The results are shown by O (good) and X (bad).

Mouthfeel (organoleptic evaluation) and taste (organoleptic evaluation) of tofu were scored by 5 expert panelists after thawing frozen tofu according to the following 5 points (5: excellent, 4: good, 3: no good, 2: somewhat bad, 1: bad). The results are shown by the average and the tofu having the score of 4 or more has marketability.

The results are shown in Table 1.

TABLE 1

| | Examples | | | | |
|---|---|---|---|---|---|
| | 1 | 2 | 3 | 4 | 5 |
| Separation of soybean milk | U | U | U | U | U |
| Soybean milk concentration (wt %) | 14 | 11 | 16 | 14 | 14 |
| Concentration of tofu | conc. | conc. | conc. | conc. | conc. |
| Soybean milk viscosity (mPa · s) | 40 | 20 | 80 | 40 | 40 |
| Amount of starch added (wt %) | 2 | 2 | 2 | 0.2 | 2 |
| Amount of transglutaminase added (wt %) | 0.1 | 0.1 | 0.1 | 0.1 | 0.01 |
| Temperature of soybean milk upon addition (° C.) | 70 | 70 | 70 | 70 | 70 |
| Coagulation reaction | O | O | O | O | O |
| Cooking applicability | O | O | O | O | O |
| Mouthfeel of tofu | 5 | 4 | 4 | 4 | 4 |
| Taste of tofu | 5 | 4 | 4 | 4 | 4 |

| | Comparative Examples | | | | |
|---|---|---|---|---|---|
| | 1 | 2 | 3 | 4 | 5 |
| Separation of soybean milk | U | U | U | C | C |
| Soybean milk concentration (wt %) | 6 | 14 | 14 | 14 | 14 |
| Concentration of tofu | no | conc. | conc. | conc. | conc. |
| Soybean milk viscosity (mPa · s) | 10 | 40 | 40 | 150 | 150 |
| Amount of starch added (wt %) | 2 | 2 | 2 | 2 | 2 |
| Amount of transglutaminase added (wt %) | 0.1 | 0.1 | 0.1 | 0.1 | 0.1 |
| Temperature of soybean milk upon addition (° C.) | 70 | 30 | 80 | 70 | 30 |
| Coagulation reaction | O | O | X | X | O |
| Cooking applicability | X | X | X | X | X |
| Mouthfeel of tofu | 1 | 3 | 1 | 2 | 2 |
| Taste of tofu | 2 | 2 | 2 | 2 | 2 |

Overall Evaluation Based on Examples 1–5, Comparative Examples 1–5 and Table 1

In view of overall evaluation, the product of Example 1 was the best and then the products of Examples 2, 3, 4 and 5 were similar to each other and better. All the products of Comparative Examples 1 to 5 were not desirable from the viewpoint of the objectives of the present invention.

EFFECT OF THE INVENTION

According to the present invention, tofu products excellent in freeze resistance can be stably produced in a industrial scale.

What is claimed is:

1. A process for producing tofu products having freeze tolerance, said process comprising adding one or more members selected from the group consisting of sugars, starch and transglutaminase to soybean milk having low viscosity and a solids content of at least 10% which has been warmed to 60° to 70° C.; adding a solidifying agent to prepare tofu; and then freezing.

2. The process according to claim 1, wherein the soybean milk is concentrated soybean milk having low viscosity which is obtained by concentrating soybean milk extracted from uncooked soybean slurry or puree prepared from whole soybeans to a solids content of 10% to 16%.

3. The process according to claim 1, wherein, after addition of the starch or the starch and one or more other additives selected from the group consisting of sugars and transglutaminase and the solidifying agent to the soybean milk, the soybean milk containing the solidifying agent is heated to elevate its temperature stepwise.

4. A tofu product obtained by the process according to claim 1.

5. The process according to claim 2, wherein, after addition of the starch or the starch and one or more other additives selected from the group consisting of sugars and transglutaminase and the solidifying agent to the soybean milk, the soybean milk is heated to elevate its temperature stepwise.

6. A tofu product obtained by the process according to claim 2.

7. A tofu product obtained by the process according to claim 3.

8. The process of claim 1, which consists essentially of adding said one or more members selected from the group consisting of sugars, starch and transglutaminase to soybean milk having low viscosity and a solids content of at least 10% which has been warmed to 60° to 70° C.; adding a solidifying agent to prepare tofu; and then freezing.

9. A tofu product produced by the process according to claim 8.

* * * * *